United States Patent [19]
Watson

[11] Patent Number: 6,006,129
[45] Date of Patent: Dec. 21, 1999

[54] ABDOMINAL EXERCISER

[76] Inventor: Steven R. Watson, 2152 Liane, Santa Ana, Calif. 92705

[21] Appl. No.: 09/081,459

[22] Filed: May 19, 1998

Related U.S. Application Data

[63] Continuation of application No. 08/547,987, Oct. 25, 1995, Pat. No. 5,755,674.

[51] Int. Cl.$^6$ ........................................ A61B 5/04
[52] U.S. Cl. ........................................ 600/546; 600/595
[58] Field of Search ................... 600/546, 595, 600/587, 552, 553, 554

[56] References Cited

U.S. PATENT DOCUMENTS

| | | | |
|---|---|---|---|
| 4,359,724 | 11/1982 | Zimmerman et al. | 340/575 |
| 4,625,733 | 12/1986 | Saynajakangas | 128/687 |
| 4,801,921 | 1/1989 | Zigentis | 340/575 |
| 4,807,692 | 2/1989 | Brown | 600/546 |
| 5,304,984 | 4/1994 | Roldan | 340/573 |

Primary Examiner—Cary O'Connor
Assistant Examiner—Pamela Wingood
Attorney, Agent, or Firm—Stetina Brunda Garred & Brucker

[57] ABSTRACT

An exercise device conveniently measures, monitors, and reports electromyograph (EMG) information to the user, for use in effectively strengthening selected muscles. The exercise device includes a sensor circuit responsive to electrical activity in tensioning muscles, and a control circuit responsive to an output signal produced by the sensor circuit. In a preferred embodiment the control circuit regulates an audio device, by attenuating the audio device output signal when the sensor output signal declines to below a preset threshold. Alternatively, the control circuit selectively activates an indication device, such as a vibrator, when the sensor output signal falls too low. The exercise device provides information as to muscle activity to the user in an entertaining fashion, and in a way that the user is not required to pay constant attention and refer to an output meter or other conventional display.

11 Claims, 2 Drawing Sheets

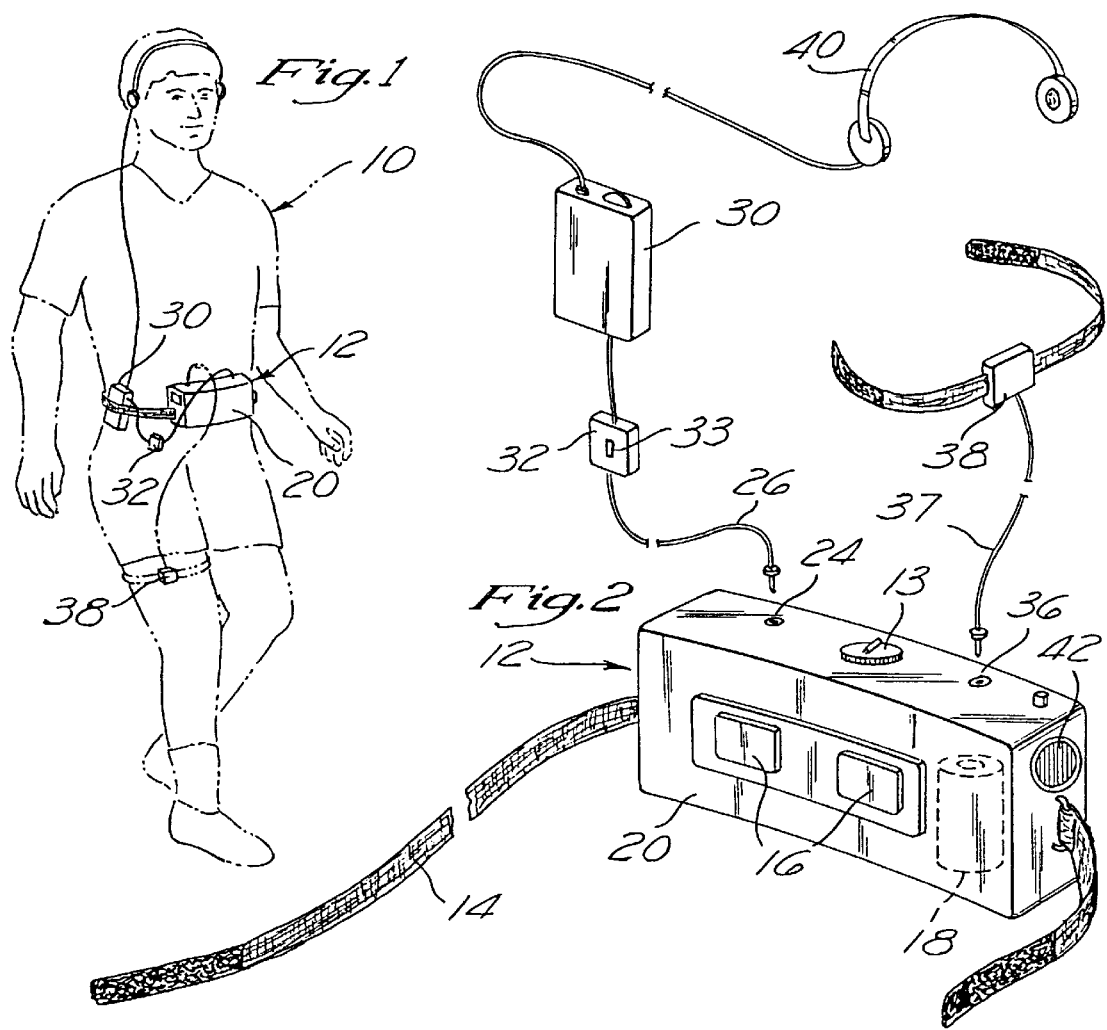
Fig. 1
Fig. 2
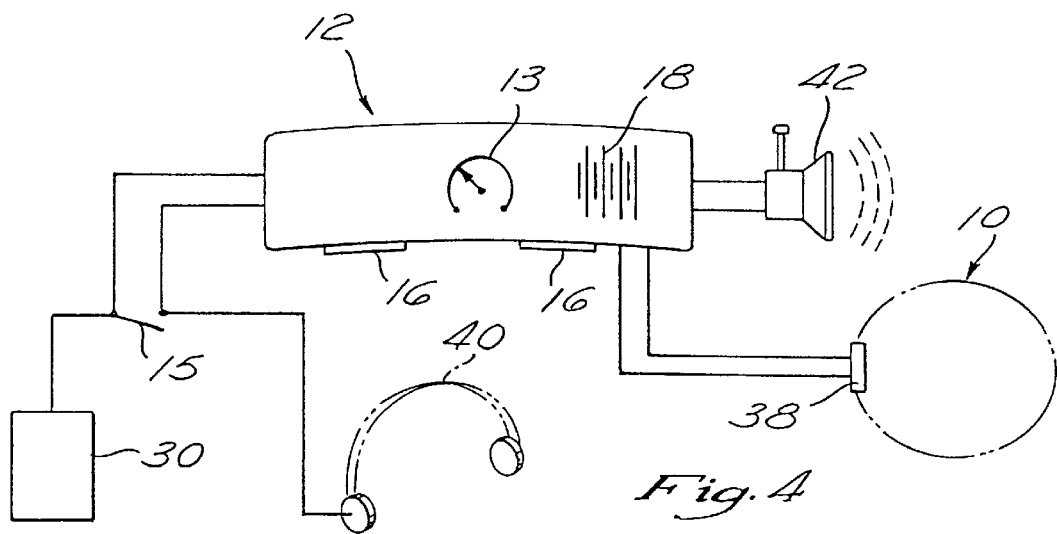
Fig. 4

ABDOMINAL EXERCISER

This application is a continuation of Ser. No. 08/547,987, filed Oct. 25, 1995, now U.S. Pat. No. 5,755,674.

FIELD OF THE INVENTION

The present invention relates to biofeedback devices and, more particularly, to electromyograph (EMG) biofeedback devices useful to monitor muscle tensioning to promote strength and functioning of muscle groups.

BACKGROUND OF THE INVENTION

The advantages of biofeedback devices are well known. By monitoring the muscle activity of the user, and providing a sensory indication of that activity, the user can learn to isolate and improve the functioning of the muscles being monitored. As a result, EMG biofeedback devices have been used for many years to help injured persons regain strength and the function of muscle groups that have impaired functionality.

Conventional EMG biofeedback devices consist of sensors applied to the body of the user adjacent the muscle area to be monitored, and a meter or similar device which displays the electrical activity of the sensor. Conventionally, as the sensed muscle activity increases, the connected meter provides an increased reading. By watching the meter the user can tell when the muscle is being contracted properly, and learn to properly control the muscle, on a repetitive basis.

EMG biofeedback devices have been used to treat urinary incontinence caused by loss of muscle tone and function. Some physical therapists utilize a small portable EMG unit with surface electrodes, along with a home exercise program, to improve problems associated with urinary incontinence.

While portable EMG biofeedback devices are currently available on the market, those devices are designed to operate in more of a clinical environment where the output meter readings are observed and correlated with muscle activity on a substantially continuous basis. As a result, it is typically difficult for a user to engage in other activities while the EMG biofeedback device is being used. Moreover, user may have little interest in using a biofeedback device which provides no entertainment value, may require constant attention to effectively utilize, and precludes completion of other tasks while the device is in use. As a result, while existing devices adequately function as EMG biofeedback units, their acceptance is limited.

The present invention addresses these deficiencies by allowing the EMG biofeedback unit to be used in a manner that does not require visual monitoring, may form a portion of an entertainment unit, and does not impede the user's ability to engage in other tasks without sacrificing the ability to monitor muscle activity. The present invention permits the biofeedback to be communicated to the user in a variety of different ways which are more advantageous to the use, enjoyment and effectiveness of the EMG biofeedback device.

SUMMARY OF THE INVENTION

The present invention comprises a muscle tensioning exercise device to improve the strength, endurance and control of selected muscles of a user. The device generally includes a sensor circuit that generates an output signal in response to sensed muscle tension, and a control circuit responsive to the sensor output signal. The control circuit regulates an audio device or other indication device, to provide information to the user as to electrical activity in his or her selected muscles.

In a preferred embodiment of the invention, the exercise device includes a headset electrically connected to an audio output device, such as a radio or compact disc player. The audio output signal is regulated by the control circuit, in response to the sensed muscle activity. The control circuit attenuates the audio output signal, when the sensor output signal falls below a preset level representing the minimal desired muscle activity. This manner of communicating the level of muscle activity to the user of the present invention has been found to provide entertainment and positively motivate individuals to exercise and tense their muscles, resulting in more rapid improvement of the physical condition of those muscles.

In an alternate embodiment, the control circuit, rather than attenuating an audio signal, activates an indication device, such as a vibrator, when the EMG actively falls below the preset threshold. Here again, the present invention communicates information concerning EMG activity to the user in a non-visual manner, allowing the user to simultaneously engage in other activities. The information is conveyed without requiring the attention of the user in continually referring to bland meter readings or other conventional output displays. As such, the tediousness of rehabilitation activity is significantly reduced, making the task of rehabilitation more palatable, and more likely.

Whether configured with the audio device, a vibrator or other sensory means such as an alarm, the present invention will benefit individuals seeking to improve isolated muscles. Heavy labor workers, fitness enthusiasts, elderly persons, women after childbirth, and individuals recovering from injuries often need and desire to improve certain isolated muscle groups, such as the abdominals. Operation and use of the present invention conveniently allows such individuals to enhance their abdominal muscles without interference with their daily routine.

These, as well as other advantages of the present invention will become more apparent from the following description and drawings. It is understood that changes in the specific structure shown and described may be made within the scope of the claims without departing from the spirit of the invention.

BRIEF DESCRIPTION OF THE DRAWINGS

FIG. 1 is a front perspective view showing two alternate embodiments of the present invention as worn by a user;

FIG. 2 is a rear perspective view of the monitoring device shown in FIG. 1, removed from the body of the user in connection with two alternate embodiments;

FIG. 4 is a schematic diagram illustrating three alternate embodiments of the present invention.

DETAILED DESCRIPTION OF THE PREFERRED EMBODIMENT

Figure 3:
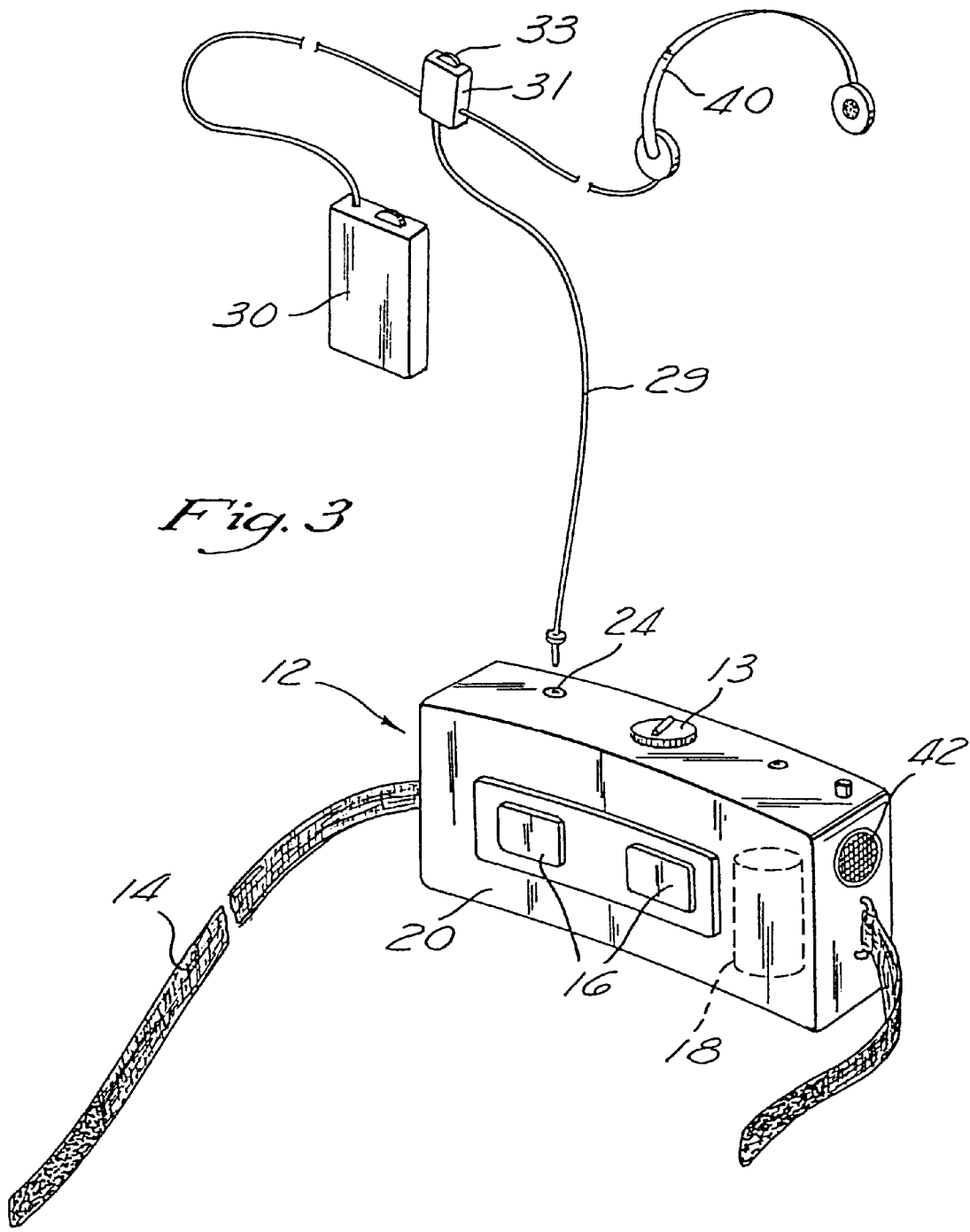
FIG. 3 is a rear perspective view of the monitoring device shown in FIG. 1, in connection with a third alternate embodiment.

The detailed description below set forth below in connection with the appended drawing is intended as a description of the presently preferred embodiment of the invention, and is not intended to represent the only form in which the present invention may be constructed or utilized. The description sets forth the functions and sequence of steps for constructing and operating the invention in connection with the illustrated embodiment. It is to be understood, however, that the same or equivalent functions and sequences may be accomplished by different embodiments that are also intended to be encompassed within the spirit and scope of the invention.

Referring to FIG. 1 of the drawings, two embodiments of the invention are shown. User 10 is shown with an abdominal monitor 12 having a sensor circuit connectable about the waist of the user 10. As shown more clearly in FIG. 2, the abdominal monitor 12 commonly includes a plurality of plate electrodes or sensors 16 disposed within a monitor housing 20. The housing 20 is preferably thin and elongate, with a contoured inner surface to match a typical user's abdominal area. The housing 20 is additionally preferably fabricated of molded plastic, offering the advantages of light weight and low cost. The housing 20 is connectable about the waist of the user 10 by a belt 14, preferably having velcro fastening means. The housing 20 may accommodate a battery 18, which powers the sensor circuit and generates a power output signal in response to the sensed muscle activity, e.g., tension.

The sensed output signal may be communicated to the user 10 in a variety of different ways. In one embodiment the sensor output signal is used to regulate power communicated to an audio device 30 via an output port 24 and a connecting cable 26. The audio device 30 may be a portable radio, cassette player, CD player, or the like. As a result of the sensed output signal the power to audio device 30 may be regulated, such that the output from the audio device 30 is completely interrupted when the sensor output signal falls before a preset level. That preset level may be adjusted by means of control such as sensor sensitivity control 13. As one of ordinary skill in the art will recognize, the precise configuration of sensitivity control 13, and the circuitry for communicating the power output signal to device 30 in response to the output of sensor 16 may be implemented in a variety of different circuit configurations, each of which is intended to be within the broader aspects of the present invention.

As shown in FIG. 2, the above-described embodiment may also incorporate an optional power control device 32 which operates to manually regulate the power provided to audio device 30. In this manner the audio device can be turned off, without the need to disconnect the device 30 from the abdominal monitor 12.

Also shown at FIG. 2 is an alternate embodiment wherein the power output of the abdominal monitor 12 is communicated to a vibrator 38 via output port 36 and connecting cable 37. In this embodiment the abdominal monitor 12 again operates to sense muscle activity and to provide power output signal when the sensed activity falls below a preset threshold, as may be established by sensitivity control 13. The power output signal in this embodiment is used to activate or deactivate a vibrator 38, which may be attached to the leg of the user 10 by means of a belt 40, preferably having velcro fastening means. This embodiment is somewhat distinguishable from the above-described embodiment insofar as the output signal from port 36 is normally in an off, or unpowered condition, subject to being powered upon sensed activity following below the preset threshold limit. As a result of falling below that preset limit, vibrator 38 is powered, causing a sensed signal to be communicated to the user. In response, the user may increase muscle activity, e.g., tensioning in the area adjacent the sensors 16, causing the vibrator to return to an off condition.

FIG. 3 illustrates yet another embodiment of the present invention, wherein the output of the abdominal monitor 12 is utilized to selectively regulate attenuation of an audio output signal, rather than regulate power to the audio device 30. As shown in FIG. 3 the output from the abdominal exerciser 12 is communicated to audio attenuation device 31, via output port 24 and connecting cable 29. Audio attenuation device 31 is provided with audio attenuation control 33, which operates to set the attenuated audio signal level that is communicated to the user's headset 40 when the sensed abdominal activity falls below the preset threshold. In this embodiment the audio signal normally communicated to the headset 40 is selectively interrupted or attenuated to a lower level in response to sensed muscle activity, without interrupting the power to device 30. As those of ordinary skill in the art will recognize, the control circuitry within abdominal exerciser 12 may be configured such that the output from port 24 may be variable in response to the degree of muscle activity of the user. As a result, audio attenuation device 31 may operate to communicate louder audio signal to the user in response to the degree of sensed muscle activity. The greater the activity, the louder the audio signal communicated to the headsets 40.

FIG. 4 illustrates an exemplary schematic that may be used in conjunction with various embodiments of the invention. As set forth therein the sensor sensitivity circuit 13 operates to regulate output of an electrical signal which controls power to the audio device 30 (FIG. 1), power to vibrator 38 (FIG. 1), or the signal to audio attenuation device 31 (FIG. 3). Accordingly, when the output of the sensor circuit 12 falls below preset thresholds, indicating that muscle tensioning has fallen below preset limits, the power to the audio indicator will be disconnected, and/or the vibration will commence and/or the audio signal will be attenuated. In another embodiment, also shown at FIG. 4, the output of abdominal exerciser 12 may be in the form of a buzzer or beeper alarm 42, which may be formed integral with the abdominal exerciser 12, as shown at FIGS. 2 and 3. The buzzer or beeping alarm 42 is similarly operative to provide an indication, in the form of an audio signal, when sensed muscle activity has fallen below a preset level. It should be understood that one or more of the output indication devices may be used simultaneously, such that, for example, when muscle activity falls below a preset limit vibrator 38 and beeping alarm 42 will both activate.

The operation, function and use of the abdominal exerciser 10 of the present invention may be further described. The housing 20 is positioned to the user 10, such that the sensors 16 are located over the selected abdominal muscles. The belt 14 is extended around the user's waist and fastened together by mating the velcro strips on the belt 14, to tightly secure the housing 20 to the user 10. Next, the audio device 30 is attached to the user's belt 14, and the connecting cable 26 plugged into the output port 24 of housing 20. Optionally a headset 40 may be placed over the user's ears and plugged into the audio device 30. Alternatively, an indication device 30 may be secured to the user's leg, or other extremity of his or her body, through use of a second belt 41.

Those of ordinary skill in the art will recognize that the present invention has a variety of additional applications. Once such application would be to assist patients with rehabilitation of back injuries by contributing to the strengthening of abdominal muscles.

Additionally, those skilled in the art will recognize that alternate or additional output devices may be utilized in conjunction with the present invention. For example, the output of the abdominal monitor 12 could be communicated (by wire connection or RF signal) to a digital wristwatch worn by the user which might provide an audio output signal in response to sensed muscle activity, and/or a digital display of some message indicative of the degree or nature of abdominal activity. Various types of sensors and sensor circuitry may be incorporated within the broader aspects of the present invention in order to selectively identify particular muscle activity and provide an indication of such activity to the user in audio or visual form. In either case, the invention allows the user to continue normal activity, without dedicating the time exclusively to rehabilitation in a clinical environment. These and other modifications and additions to the present invention will be apparent to those skilled in the art and may be implemented for use in a variety of different applications without departing from the broader aspects of the present invention.

What is claimed is:

1. An abdominal tensioning device for promoting the tensioning of abdominal muscles of a user, the device comprising:

a) an indicator device for generating an indicator output signal;

b) an abdominal electrical activity monitor having at least one sensor disposed upon an outer surface thereof, said sensor being operative to detect electrical signals representative of a users level of abdominal contraction, the monitor being operative to generate a monitor output signal in response to the level of detected electrical signals, and to attenuate the monitor output signal when the level of detected electrical signals fall below a preset threshold, the monitor being formed to be disposable upon the user's body adjacent the abdominal muscles of the user; and c) a sensor sensitivity circuit for adjusting the preset threshold;

d) wherein the indicator device is operative to generate an indicator output signal when the detected electric signals fall below the preset threshold.

2. The device as recited in claim 1, further comprising a belt for securing the abdominal monitor about the user's waist.

3. The device as recited in claim 1, wherein the indicator device comprises a vibrator for providing a vibration indication when the detected electrical activity falls below the preset threshold.

4. The device as recited in claim 3, wherein the sensor sensitivity circuit is operated to terminate vibration of the vibrator when the detected electrical signals increase above the preset threshold.

5. The device as recited in claim 1, wherein the indicator device comprises an audio device for providing a audio indication when the detected electrical signals falls below the preset threshold.

6. The device as recited in claim 5, wherein the sensor sensitivity circuit is operated to terminate the audio indication when the detected electrical signals increase above the preset threshold.

7. The device as recited in claim 1, wherein the indicator device comprises a visual display device for providing a visual indication when the detected electrical signals falls below the preset threshold.

8. The device as recited in claim 7, wherein the sensor sensitivity circuit is operated to terminate the visual indication when the detected electrical signals increase above the preset threshold.

9. The device as recited in claim 1, wherein the sensor is operative to continually detect electrical signals representative of the users ongoing level of abdominal contraction, and to generate a first output signal when the user's abdominal muscles are relaxed and a second output signal when the user's abdominal muscles are contracted.

10. The device as recited in claim 1, wherein the monitor is operative to progressively attenuate a monitor output signal in response to the level of contraction of the user's abdominal muscles.

11. The device as recited in claim 9, wherein the monitor is contoured to conform to the user's abdominal area.

* * * * *